United States Patent [19]

Osterhoudt et al.

[11] Patent Number: 5,149,416
[45] Date of Patent: Sep. 22, 1992

[54] POLYMERIC ELECTROPHORESIS MEDIA

[75] Inventors: Hans W. Osterhoudt, Spencerport; Ignazio S. Ponticello, Pittsford; Kenneth G. Christy, Jr.; David B. LaTart, both of Rochester, all of N.Y.

[73] Assignee: Eastman Kodak Company, Rochester, N.Y.

[21] Appl. No.: 812,885

[22] Filed: Dec. 20, 1991

Related U.S. Application Data

[63] Continuation of Ser. No. 431,048, Nov. 2, 1989, abandoned, which is a continuation-in-part of Ser. No. 339,468, Apr. 18, 1989, abandoned.

[51] Int. Cl.$^5$ ................. G01N 27/26; R01D 57/02
[52] U.S. Cl. ............................. 204/299 R; 204/182.8; 204/180.1
[58] Field of Search ............ 204/299 R, 182.8, 182.9, 204/180.1

[56] References Cited

U.S. PATENT DOCUMENTS

| 3,966,897 | 6/1976 | Renn et al. | 436/515 |
|---|---|---|---|
| 4,048,377 | 9/1977 | Boschetti et al. | 524/56 X |
| 4,094,832 | 6/1978 | Söderberg | 526/238.2 X |
| 4,504,641 | 3/1985 | Nochumson | 526/238.2 |
| 4,542,200 | 9/1985 | Nochumson | 526/238.2 |
| 4,548,869 | 10/1985 | Ogawa et al. | 204/182.8 X |
| 4,548,870 | 10/1985 | Ogawa et al. | 204/182.8 X |
| 4,582,868 | 4/1986 | Ogawa et al. | 204/182.8 X |
| 4,596,858 | 6/1986 | Gregor et al. | 525/328.2 |
| 4,600,641 | 7/1986 | Ogawa et al. | 204/182.8 X |
| 4,737,533 | 4/1988 | Charmot et al. | 524/22 |
| 4,769,408 | 9/1988 | Ogawa et al. | 204/182.8 X |

Primary Examiner—John Niebling
Assistant Examiner—John S. Starsiak, Jr.
Attorney, Agent, or Firm—Irving Newman

[57] ABSTRACT

Preformed, water-soluble, acrylamide based copolymers comprising a minor proportion of a comonomer, which comonomer contains a site for a crosslinking reaction with a selected crosslinking agent by a reaction that does not involve a free-radical vinyl addition mechanism, which copolymers have $\overline{M}_w$ and $\overline{M}_n$ values within selected ranges, can be conveniently and safely used to prepare electrophoresis gel media in situ.

31 Claims, No Drawings

POLYMERIC ELECTROPHORESIS MEDIA

CROSS REFERENCE TO RELATED APPLICATIONS

This is a continuation of copending application Ser. No. 07/431,048 filed on Nov. 2, 1989 now abandoned, which is a continuation-in-part of U.S. application Ser. No. 339,468, filed Apr. 18, 1989, now abandoned. It is also related to the subject matter of application Ser. Nos. 188,821, filed May 2, 1988 now U.S. Pat. No. 4,948,480; 339,350, filed Apr. 18, 1989 now abandoned; 339,456, filed Apr. 18, 1989 now abandoned; 339,469, filed Apr. 18, 1989 now abandoned and continuations or continuations-in-part of these applications being filed concurrently herewith.

FIELD OF THE INVENTION

This invention relates to a medium or element for electrophoresis. More particularly, it relates to improved polymeric gel media suitable for electrophoretic separation of biopolymers such as proteins and polynucleic acids (DNA, RNA and their derivatives or fragments).

DESCRIPTION RELATIVE TO THE PRIOR ART

U.S. Pat. No. 4,704,198, which issued on Nov. 3, 1987, contains a comprehensive description of various aspects of electrophoresis. As described therein, and in numerous other publications, electrophoresis is based on the principle that charged molecules or substances will migrate when placed in an electric field. Since proteins and other biopolymers (e.g., DNA, RNA, enzymes and some carbohydrates) are charged, they migrate at pH values different from their isoelectric points. The rate of migration depends, among other things, upon the charge density of the protein or biopolymer and the restrictive properties of the electrophoretic matrix or medium. The higher the ratio of charge to mass, the faster an ion will migrate. The more restrictive the medium, the more slowly an ion will migrate. Electrophoresis has the further advantage of generally requiring only very small (i.e., microgram or less) quantities of material for analysis.

Electrophoresis is generally performed in an aqueous solution or gel across which a voltage is applied. It is the voltage gradient that causes the migration of the species being separated. Gradients typically range from 10 volts/cm to many times higher, the magnitude depending on the nature of the separation being formed.

In theory, separation of different proteins could be achieved readily in free solution provided that the molecules differed sufficiently in their charge densities. However, in practice, separations in free solution are difficult to achieve because convective disturbances produced by or occurring during electrophoresis cause distortions of the protein bands. Resolution of the individual proteins is compromised because the bands are broadened. Also, band broadening continues even after the electrophoresis has been stopped because of diffusion of dissolved solute. Therefore, electrophoresis in free solution is rarely performed. In practice, various supporting media are used to minimize convection and diffusion, and to effect separation both on the basis of molecular size and of net charge.

Many support media for electrophoresis are in current use. The most popular are sheets of paper or cellulose acetate, agarose, starch, and polyacrylamide. Paper, cellulose acetate, and similar porous materials are relatively inert and serve mainly for support and to minimize convection. Separation of proteins using these materials is based largely upon the charge density of the proteins at the pH selected.

On the other hand, starch, agarose and polyacrylamide gels not only minimize convection and diffusion but also actively participate in the separation process. These materials provide a restrictive medium in which the average size of the polymeric network opening (or average pore size) can be controlled to achieve a molecular fractionation in a desired molecular size range. In this way, molecular sieving occurs and provides separation on the basis of both charge density and molecular size.

The extent of molecular sieving is thought to depend on how much the gel network opening size (i.e., average pore size) is larger than the size of the migrating particles. The average pore size of agarose gels is so large that molecular sieving of most protein molecules is minimal and separation of proteins in that medium is based mainly on charge density. In contrast, polyacrylamide gels can have openings whose sizes more closely approximate the sizes of protein molecules and so contribute to the molecular sieving effect. Polyacrylamide has the further advantage of being a synthetic polymer which can be prepared in highly purified form.

With agarose, a polysaccharide, the gel is formed by casting a heated (T > 50° C.) agarose solution and allowing the solution to cool. This process of gelation on cooling is similar overall, and even on a molecular basis, to the formation of gelatin gels from cooled solutions of gelatin in water. Agarose is rarely used at concentrations higher than 5% because such solutions are very viscous and not easily poured. Agarose is therefore widely used at concentrations <5% (w/v) for the electrophoresis of large molecules, e.g., high molecular weight proteins, and polynucleotides.

The ability to produce gels having a wide range of polymer concentrations (and, therefore, since the gel network opening decreases with increasing polymer concentration, a wide range of controlled average pore sizes) as well as to form pore size gradients within the gels by virtue of polymer concentration gradients, are additional advantages of polyacrylamide as an electrophoresis gel medium. Control over pore size enables mixtures to be sieved on the basis of molecular size and enables molecular weight determinations to be performed. These determinations are especially accurate if the proteins are treated with a detergent, such as sodium dodecyl sulfate (SDS), which neutralizes the effects of inherent molecular charge so that all SDS treated molecules, regardless of size, have approximately the same charge density values. This technique is referred to as SDS-PAGE (Sodium Dodecyl Sulfate-PolyAcrylamide Gel Electrophoresis).

The popularity of polyacrylamide-based electrophoresis gels stems not only from the comparatively wide latitude in polymer content and buffer composition attainable with them, but also from the high degree of inertness in the gel with respect to both the voltages applied and the solutes being separated, the ease with which proteins are detected once separated and good reproducibility with carefully prepared gels.

Conventionally, polyacrylamide gel media for use in SDS-PAGE electrophoresis have been prepared in situ by free radical induced polymerization of a monomer such as acrylamide and a crosslinking agent, most commonly N,N'-methylenebisacrylamide, under oxygen-free conditions in the presence of water, a buffer, a polymerization initiator, and a polymerization catalyst. More particularly, since such polymerization can be inhibited by the presence of oxygen, polyacrylamide gel media for electrophoresis typically are prepared by a process involving: introducing a previously deoxygenated aqueous solution containing acrylamide, a crosslinking (bis) monomer, a buffer, a free radical polymerization initiator and a polymerization catalyst into a cell formed between two glass plates with a selected clearance (e.g., 0.15-3 mm); and sealing the gel-forming solution from oxygen; whereupon the free radical polymerization proceeds so as to prepare the desired gel. Often this is done in situ by the scientist who is to conduct the electrophoresis.

The usual practice is to perform a free radical polymerization with acrylamide and a suitable bis monomer such as N,N'-methylenebisacrylamide (often simply referred to as "bis") in order to obtain a gel. Such gel formation is successfully done only as several precautions are taken, namely: (a) very high purity starting materials should be used; (b) the solution of monomers and buffer should be degassed to remove oxygen; (c) a free radical initiator and a catalyst must be quickly mixed into the degassed solution; (d) the solution should be quickly poured between two glass plates or down a glass tube, the lower end of which in either case is sealed to prevent leakage; and (e) the gelation should proceed with (i) oxygen largely excluded and (ii) adequate means for heat dissipation being present so that excess heat does not cause gel nonuniformities.

The cell employed for the preparation of the gel generally has a length of approximately 6 to 60 cm. Accordingly, the introduction of the gel-forming solution into such a long cell requires careful operation to prevent the solution from gelling before it is completely poured (which would prevent the preparation of a uniform polyacrylamide gel medium of the desired length). Thus, the preparation of a polyacrylamide gel medium for electrophoresis having the desired dimensions and consistency requires a great deal of skill and care, as well as keeping the solution free from oxygen.

Precautions are also required in handling the monomers since both acrylamide and bis have been identified as known neurotoxins and suspected carcinogens.

There are several alternatives to the above-described procedure whereby the user makes electrophoresis gels by free radical polymerization and crosslinking in situ. These include (a) the use of preformed gels in cassettes and (b) the use of preformed gels on flexible supports. With either of these alternatives, however, some operating freedom or flexibility with regard to gel size, polymer content in the gel and buffer content is lost. Also—especially with precast gels in cassettes made by free radical polymerization and crosslinking—there generally remain, after completion of the gel formation reaction, some unreacted monomers, initiator by-products and catalyst. The presence of such species poses some toxicological hazards to the user and may interfere with the electrophoretic separation to be performed. Also, such precast gels have been found to have limited shelf lives.

U.S. Pat. No. 4,582,868, among others, describes the crosslinking of acrylamide-rich copolymers to form electrophoresis gel media by a non-free radical induced mechanism that does not require exclusion of oxygen. Typically, copolymers of acrylamide and a monomer that affords sites for subsequent non-free radical initiated crosslinking by treatment with a crosslinking agent, for example, an acrylamide derivative such as N-[3-(2-chloroethylsulfonyl)propionamidomethyl]acrylamide,

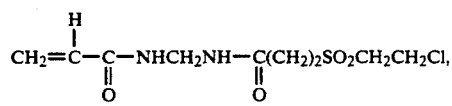

an acrylate derivative such as 2-[3-(2-chloroethylsulfonyl)propionyloxy]ethyl acrylate,

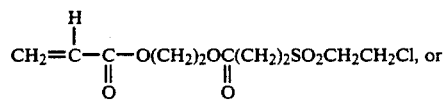

an active ester such as N-[2-(ethoxycarbonylmethoxycarbonyl)ethyl]acrylamide:

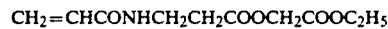

are prepared, in accordance with U.S. Pat. No. 4,582,868, by a free radical initiated polymerization in the absence of oxygen. Thereafter, in a separate procedure, which can safely be performed in the presence of oxygen, the chloroethylsulfonyl or other pendent reactive group-containing polymers are crosslinked by reaction at a suitable pH with a bis-nucleophile crosslinking agent such as a diamine or a dithiol. In this regard, it is noted that electrophoresis often is performed at pH values that facilitate dehydrohalogenation of the chloroethylsulfonyl groups. If the vinylsulfonyl groups so formed are not all reacted with the intended crosslinking agent, they could react with amino groups on dissolved proteins during electrophoresis. Such reaction would artifactually retard the electrophoretic migration of proteins and consequently give misleading electrophoresis results vis-a-vis the results obtained with electrophoresis gels formed by the free radical polymerization of acrylamide and bis alone. Therefore, enough crosslinking agent should be used to assure complete reaction of these groups.

Despite the availability of the above-described alternatives, electrophoresis media are still generally prepared by the polymerization of vinyl monomers at the time of use. This necessarily involves exposure of the operator to monomers prior to use and to residual monomers during use. Such monomers are suspected carcinogens, and at least some are known to be neurotoxins.

Although bis is the most widely used crosslinker for acrylamide-based electrophoresis gels, bis-crosslinked gels generally cannot be resolubilized. The ability to solubilize the gel after performing electrophoresis is advantageous in that it enables one to recover a resolved species from the gel. The use of an alternative, cleavable crosslinker such as diallyltartardiamide (DATD)

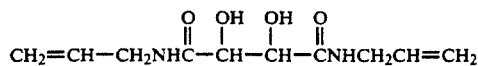

permits the researcher to achieve such recovery. After electrophoresis, each portion of the gel to be solubilized is excised and treated in a dilute solution of periodic acid. The —CHOH—CHOH— linkage in the middle of the crosslink is cleaved in the periodic acid solution and a solution of the thus solubilized polymer is produced. From this solution one can easily recover the resolved species for further experiments. Obviously, it would be advantageous to provide researchers with the option of gel solubilization after electrophoresis.

Also, if electrophoresis is to be performed soon after gelation, the chemical reaction (i.e., crosslinking) responsible for gelation must be compatible with the buffers present for electrophoresis. Gel electrophoresis is often performed at pH values ranging from 5 to 9.

A particularly popular system for the determination of molecular weights of proteins by electrophoresis was described by Laemmli, Nature, 227:680 (1970). In this system, two gels are used, one directly above the other, with a multi-phasic buffer system. The upper (or stacking) gel is at pH 6.8, which is achieved with tris(hydroxymethyl)aminomethane to which HCl has been added to lower the pH. The stacking gel has a low polymer concentration (generally from 4 to 6% w/v). Its purposes are (a) to provide a medium onto which samples can be loaded in discrete lanes and (b) to concentrate all species in a particular sample at the interface between the stacking gel and the lower (or resolving) gel. In meeting objective (b), the solutes, which are generally sodium dodecylsulfate (SDS)-denatured proteins, are "stacked" together (or very nearly so) i.e., are concentrated at the interface of the two gels, just before entering the resolving gel. For the stacking to occur effectively, the proteins, rather than the buffer, should carry most of the current and there should be no molecular size separation.

Molecular size separation occurs in the resolving gel, where the buffer carries most of the current and the solutes migrate at a velocity determined by the voltage gradient and the retardation due to the pore size distribution of the crosslinked polymer gel. The pH in the resolving gel is typically 8.8 and the polymer concentration is usually at least 10% (w/v).

In summary, the popular Laemmli procedure requires two gels, the lower of which (resolving gel) is larger (thereby providing a longer path for solutes to tranverse) and contains a higher concentration of the gelled polymer, and therefore a smaller average pore size than that of the upper, or stacking gel. The conditions recommended by Laemmli are:

|  | Stacking Gel | Resolving Gel |
| --- | --- | --- |
| pH | 6.8 | 8.8 |
| buffer | 0.125M Tris.HCl | 0.375M Tris.HCl |
| gel conc., % (w/v) | 4–6 | >10 |

Despite the various advances in electrophoresis technology, there is still a need for further improvements so that one not only can coat the solutions to be gelled in the presence of oxygen but also can easily and safely (a) pour such solutions into tubes or between plates, (b) form gels quickly and (c) solubilize gels or portions thereof for example recovery after electrophoresis.

SUMMARY OF THE INVENTION

The present invention provides more convenient, safer means than were heretofore available for preparing an acrylamide-based electrophoresis gel that permits the operator to overcome several disadvantages found in the prior art. In accordance with the present invention, we have discovered that the weight average molecular weight $\overline{M}_w$ and the number average molecular weight $\overline{M}_n$ are among the critical parameters that must be properly selected in order for a preformed polymer that is subsequently crosslinked with a chemical crosslinking agent that does not involve a free-radical vinyl addition mechanism, first to produce a gellable polymer solution for forming a resolving electrophoresis gel that (1) is easily poured into a slot (mold, tube, or between glass plates) no greater than 0.15 cm thick, (2) has a short gel time (i.e., about 4 to 10 minutes; by "gel time" is meant the time from addition of the crosslinking agent until the solution cannot be poured easily), but (3) remains pourable into said slot for a sufficient time to fill an electrophoresis mold of $14 \times 14 \times 0.15$ cm (which takes about 4 to 6 minutes); and second, within about 10 minutes to 2 hours after addition of the crosslinking agent, to produce a firm gel having (1) sufficient crosslink density to afford good molecular sieving during electrophoresis, (2) good resolution during electrophoresis, and (3) sufficient physical integrity to permit manual removal of the hardened gel from the mold shortly after electrophoresis as well as its handling without causing detrimental flow, compression, fracture, strech, tear, or disintegration of the gel.

The requirements of $\overline{M}_w$ and $\overline{M}_n$ in said preformed polymer component of the electrophoresis media are:

1) $\overline{M}_w$ is small enough that the addition of 1.25 to 1.5 times the stoichiometric amount of the selected crosslinking agent will not raise the viscosity of the mixture so much that the media cannot be poured into a $0.15 \times 14 \times 14$ cm mold within about 4 to 10, preferably about 6 to 8 minutes after addition of the crosslinking agent, 2) $\overline{M}_n$ is enough to provide a crosslink density sufficient to form a gel after about 10 minutes after addition of 1.25 to 1.5 times the stoichiometric amount of the selected crosslinking agent, said gel ultimately having sufficient integrity within about 2 hours after pouring to be removed from the mold and handled gently without tearing or falling apart, and 3) the number of equivalents of crosslinking sites per gram of polymer is in the range of $0.45(10^{-4})$ to $14(10^{-4})$, preferably at least $2/\overline{M}_n$; more preferably from about $2.25(10^{-4})$ to $10(10^{-4})$, most preferably about $4(10^{-4})$ to $7(10^{-4})$.

More particularly, a copolymer of the present invention for preparing a resolving gel for electrophoresis is a water soluble vinyl addition copolymer derived from a mixture of monomers comprising from 85–98 mole percent, preferably 90 to 97 mole % of a monomer selected from acrylamide and the (N-substituted acrylamides wherein the N-substituent is an alkyl group having from 1 to 5 carbon atoms, from 2 to 15 mole percent, preferably 3 to 10 mole percent, of a vinyl monomer having a reactive group selected from the group consisting of a) active halogen groups; b) activated 2-substituted ethylsulfonyl or activated vinylsulfonyl groups; c) epoxy groups; d) isocyanate groups; e) aziridine groups; f) aldehyde groups; g) 2-substituted ethylcarbonyl groups; and h) succinimidoxycarbonyl groups; and from 0 to 12 mole percent of one or more other polymerizable nonionic vinyl monomers selected from styrene monomers, acrylic monomers, methacrylamide monomers and N-substituted acrylamide monomers wherein the substituent contains at least 6 carbon atoms, said water soluble copolymer having a number average molecular weight, $\overline{M}_n$, of at least about 7,000, preferably from about 7,000 to about 30,000, and a weight average molecular weight, $\overline{M}_w$, of less than about 100,000, preferably from about 25,000 to about 100,000.

In another aspect, this invention also relates to a new stacking gel composition comprising polymers of the same chemical composition as described for the resolving gel but having a much greater value for $\overline{M}_w$. $\overline{M}_n$ is also generally higher but this parameter is not as critical as $\overline{M}_w$ in the copolymer for the stacking gel. These molecular weights are each significantly higher than those of the resolving gel when polymers of exactly the same chemical composition are used. The $\overline{M}_n$ is preferably greater than about 50,000 and $\overline{M}_w$ is greater than about 100,000, preferably greater than about 150,000. The gel time is somewhat longer than that of the resolving gel because stacking gels are formed at a lower concentration (4-6% vs about 12%) and a lower pH (6.0-8.0) than resolving gels.

In yet another embodiment, the copolymer of the present invention, whether in the form of a resolving gel, stacking gel or both, is provided in a kit for preparing an electrophoresis gel, this kit comprising the copolymer and, in a separate container from the copolymer, a suitable crosslinking agent for crosslinking the copolymer by a reaction that does not involve a free-radical initiated vinyl addition mechanism. Optionally, the kit may also contain a selected buffer and other suitable ingredients for incorporation into the electrophoresis medium.

DETAILED DESCRIPTION OF THE INVENTION

A preferred preformed crosslinkable polymer useful for preparing a resolving gel for electrophoresis in accordance with this invention is poly[acrylamide-co-N-(3-chloroacetamidopropyl)methacrylamide] (weight ratio of acrylamide to comonomer: 90/10; mole ratio: 96.5/3.5) used at a concentration of about 12% (w/v) in the gel. It has a preferred $\overline{M}_w$ of about $4.6 \times 10^4$; a preferred $\overline{M}_n$ of about $1.7 \times 10^4$; and preferably about $4.59 \times 10^{-4}$ equivalents of crosslinking site per gram.

In addition to the above preferred polymer, any water-soluble vinyl addition acrylamide copolymer having the requisite $\overline{M}_w$, $\overline{M}_n$, and equivalents of crosslinking site per gram of polymer would be useful in the practice of this invention, especially copolymers of the structure:

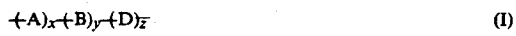

wherein
—A— represents recurring units derived from acrylamide and N-substituted acrylamide wherein said substituent has less than about 6 carbon atoms;
—B— represents recurring units derived from vinyl monomers containing crosslinkable sites selected from:
a) active halogen groups;
b) activated 2-substituted ethylsulfonyl or activated vinylsulfonyl groups;
c) epoxy groups;
d) isocyanate groups;
e) aziridine groups;
f) aldehyde groups;
g) 2-substituted ethylcarbonyl groups; and
h) succinimidoxycarbonyl groups;
—D— represents recurring units derived from any other nonionic monomers including styrene monomers, acrylic monomers, methacrylamide monomers, and substituted acrylamide monomers wherein said substituents have 6 or more carbon atoms; and x, y, and z represent mole percents, x being 85 to 98, preferably 90 to 97 mole %; y being 2 to 15, preferably 3 to 10 mole % and z being 0 to 12, preferably 0 to about 3 mole %.

Examples of suitable acrylamide monomers (A) for inclusion in the copolymers of the present invention include acrylamide, N-isopropylacrylamide, N-hydroxymethylacrylamide, N-(1,1-dimethyl-3-oxobutyl)acrylamide, N-methylmethacrylamide, 2-acrylamido-2-hydroxmethyl-1,3-propanediol, methacrylamide, 3-(3-dimethylaminopropyl)acrylamide, N,N-dimethylacrylamide, N,N-diethylacrylamide, N-isopropylmethacrylamide, and 3-(2-dimethylaminoethyl)acrylamide. Particularly preferred is (unsubstituted) acrylamide.

The —B— recurring units can contain any of the reactive groups a) to h) to provide the required concentration of sites for crosslinking for preparing electrophoresis gel media in accordance with the invention. All of these groups react readily with difunctional or polyfunctional amino and/or sulfhydryl group-containing crosslinking agents.

While free or ionized pendent carboxyl groups could afford crosslinking sites on the polymer, they should be avoided because, being ionic, any unreacted carboxyl groups (or other ionic groups) could interfere with electrophoretic separations in SDS-PAGE electrophoresis.

One preferred class of monomers which provide the requisite reactive groups is the monomers containing an active halogen atom which readily reacts with amine and sulfhydryl groups. Examples of monomers having an active halogen atom include vinyl chloracetate, vinyl bromoacetate, haloalkylated vinyl aromatics (for example, chloromethylstyrene and bromomethylstyrene), haloalkyl acrylic and methacrylic esters (for example, chloroethyl methacrylate, 3-chloro-2-hydroxypropyl methacrylate and 3-chloropropyl acrylate), N-(3-chloroacetamidopropyl)methacrylamide, 2-chloroacetamidoethyl methacrylate, 4-chloroacetamidostyrene, 3- and 4-chloroacetamidomethylstyrene, N-[3-(N'-chloracetylureido)propyl]methacrylamide, 2-(N'-chloroacetylureido)ethyl methacrylate, 4-(N'-chloroacetylureido)styrene, 4-(N'-chloroacetylureidomethyl)styrene, and others known to those skilled in the art.

Another useful class of monomers comprises those having activated 2-substituted ethylsulfonyl and vinylsulfonyl groups. A number of representative monomers having the latter groups are known in the art, including those disclosed in U.S. Pat. Nos. 4,161,407 and 4,548,870.

Preferred activated 2-substituted ethylsulfonyl and vinylsulfonyl monomers can be represented by the formula (II):

wherein R is hydrogen or substituted or unsubstituted alkyl (generally of 1 to 6 carbon atoms, such as methyl, ethyl, isopropyl or hexyl). Preferably, R is hydrogen or methyl.

$R^1$ is —CH=$CHR^2$ or —$CH_2CH_2X$ wherein X is a leaving group which is displaced by a nucleophile or is eliminated in the form of HX by treatment with a base (such as halo, acetoxy, alkylsulfonyloxy such as methylsulfonyloxy, arylsulfonyloxy such as p-tolylsulfonyloxy, and trialkylammonio, for example, a trimethylammonio salt, or a pyridinio salt). $R^2$ is hydrogen, substituted or unsubstituted alkyl (generally of 1 to 6 carbon atoms as defined for R), or substituted or unsubstituted aryl (generally of 6 to 12 ring carbon atoms, such as phenyl, naphthyl, xylyl or tolyl). Preferably, $R^1$ is —$CH_2CH_2X$. This group, which is an activated 2-substituted ethyl group, can be substituted with any group which does not impair the displacement of the leaving group X.

L is a linking group which can be a substituted or unsubstituted alkylene generally having 1 to 20 carbon and hetero atoms in the backbone. This definition of alkylene is meant to include alkylene groups interrupted or terminated with oxy, thio, —$NR^3$— [wherein $R^3$ is hydrogen, substituted or unsubstituted alkyl of 1 to 6 carbon atoms (such as methyl, chloromethyl or 2-hydroxyethyl) or substituted or unsubstituted aryl of 6 to 12 carbon atoms (such as phenyl, naphthyl, xylyl, or tolyl)], ester (—COO—), amide (—CONH—), urylene

(—NHCNH—), sulfonyl (—$SO_2$—), carbonate, sulfonamide, azo, phosphono or other similar groups. Representative alkylene groups include methylene, ethylene, isobutylene, hexamethylene, carbonyloxyethoxycarbonyl, methylenebis(iminocarbonyl), carbonyloxydodecylenecarbonyloxyethylene, carbonyliminomethyleneiminocarbonyliminoethylene, carbonyliminomethyleneiminocarbonylethylene and other groups described or suggested by U.S. Pat. Nos. 4,161,407 and 4,548,870, noted above.

L can also be substituted or unsubstituted arylene generally having 6 to 12 ring carbon atoms. Representative arylene groups include phenylene, tolylene, naphthylene and others noted in the patents mentioned above. Also included in this definition of L are divalent groups which are combinations of one or more of each of the alkylene and arylene groups defined above (for example, arylenealkylene, alkylenearylenealkylene and others readily determined by one of ordinary skill in the art). Preferably L is unsubstituted phenylenealkylene, phenylenealkylene substituted with one or more alkyl groups (as defined for R), alkoxy groups (generally of 1 to 6 carbon atoms, for example, methoxy, propoxy or butoxy) or halo groups, or carbonyliminomethyleneiminocarbonylethylene.

Representative 2-substituted ethylsulfonyl and vinyl sulfonyl monomers from which —B— can be derived include m and p-(2-chloroethylsulfonylmethyl)-styrene, m and p- [2-p-tolylsulfonyloxy)ethylsulfonylmethyl]styrene, m and p-vinylsulfonylmethylstryene, N-[p-(2-chloroethylsulfonylmethyl)phenyl]acrylamide, and N-[2-(2-chloroethylsulfonyl)ethylformamidomethyl]acrylamide.

Other monomers which can be incorporated in the polymers to provide the requisite reactive groups include monomers containing epoxy groups (such as glycidyl acrylate, glycidyl methacrylate, vinyl glycidyl ether or methallyl glycidyl ether), monomers containing isocyanate groups (such as isocyanatoethylacrylate, isocyanatoethyl methacrylate, or α,α-dimethylmetaisopropenylbenzyl isocyanate), monomers containing an aziridine group [such as vinylcarbamoylaziridine, acryloylaziridine, methacryloylaziridine, and 2-(1-aziridinyl)ethyl acrylate], monomers containing aldehyde groups (such as vinyl benzaldehyde or acrolein), or 2-substituted ethylcarbonyl containing monomers (such as 2-chloroethyl acrylate, 2-chloro-ethyl methacrylate, 2- methylsulfonyloxyethyl methacrylate, and 2-p-tolylsulfonyloxyethyl acrylate).

The foregoing polymers can be crosslinked with agents having two or more amino, mercapto, sulfinic acid, or phenolic hydroxy groups such as ethylenediamine, 1,3-propanediamine, 1,3-propanedithiol, dithiothreitol, dithioerythritol, 1,5-pentanediamine, hexamethylenediamine, diethylenetriamine, triethylenetetramine, propylenediamine, di(aminomethyl)ether, 1,8-diamino-4-(aminomethyl)octane, xylylenediamine, hydroquinone, bisphenol A, bisphenol sulfone, 1,4-butanedisulfinic acid, benzenedisulfinic acid, thioethanolamine, p-aminothiophenol, and butylenediamine.

Our preferred reactive group for —B— is the chloroacetyl, especially in the form of a chloroacetamido group. This group is electrophilic and would be expected to react with a nucleophile such as an amine or a thiol. We have found that the reaction with a thiol occurs much more rapidly than with an amine at the pH values (7-10) of most interest for electrophoresis. Thus we have found in one preferred embodiment that dithiothreitol (DTT), $HSCH_2(CHOH)_2CH_2SH$, is a very effective crosslinking agent for this class of polymers. The advantages of DTT, besides the rapid crosslinking reaction even in the presence of a primary amine (Tris buffer), include (a) water solubility, (b) low toxicity, and (c) susceptibility to post-electrophoresis reaction with periodic acid to solubilize the gel or selected portions thereof.

The chloroacetamido-thiol reaction is pH sensitive and produces HCL as a by-product of the reaction:

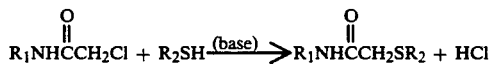

Consequently, we have found it advantageous to adjust to 7.8 and 9.4, respectively, the pH's of the Tris·HCl solutions used in the stacking gel and resolving gel buffers. These adjustments increase the rate of reaction and compensate for the generation of HCl. We have found that the electrophoretic separation of SDS-complexed proteins on DTT crosslinked poly[acrylamide-co-N-(3-chloroacetamidopropyl)methacrylamide] copolymers compares very favorably to the separation obtained on acrylamide/bis gels.

Selection and incorporation of suitable buffer is well within the knowledge of skilled workers in the electrophoresis art and depends upon the materials to be separated by the electrophoresis process in which the medium is to be employed. Such buffers and bases for selecting them are described, for example, in Andreas Chrambach, "The Practice of Quantitative Gel Electrophoresis," VCH Publishers, Deerfield Beach, Fla., U.S.A. (1985), and U.K. Laemmli, Nature, 227:680, (1970).

The preferred units —B— bearing the chloracetamido group (as is true for any recurring unit —B— in the polymers of the present invention) should be present only to the extent needed to provide the desired degree of crosslinking density in the polymeric gel. Less than the necessary amount would lead to gels in which the crosslink density is too low, whereas greater amounts than needed would detract from the acrylamide-like character that we seek. We have found that the crosslink density and molecular weight requirements are satisfied if the copolymer contains on a weight basis 10% N-(3-chloroacetamidopropyl)methacrylamide monomer (on a mole basis this is 3.5% N-(3-chloroacetamidopropyl)methacrylamide).

With 10% (by weight) N-(3-chloroacetamidopropyl)methacrylamide in the resolving gel ($G_R$) copolymer, the number of equivalents of crosslinking site per gram (y) can be computed as $$y = \frac{0.10}{218} = 4.59(10^{-4})$$

Knowing y and the molecular weight between crosslinks ($\overline{M}_c$) desired permits the estimation of the minimum value of $\overline{M}_n$ for the starting copolymer consistent with achieving the crosslink density sought.

$$\frac{1}{\overline{M}_n} = \frac{y}{2} - \frac{1}{\overline{M}_c} = 2.30(10^{-4}) - \frac{1}{5.8(10^3)}$$

$$\overline{M}_n = 1.7(10^4)$$

The preferred weight average molecular weight $\overline{M}_w$ is not estimated so directly. We have found, nevertheless, that the elapsed time necessary to form a gel after addition of crosslinking agent to an aqueous solution of polymer in accordance with the invention decreases with increasing $\overline{M}_w$ (as expected) and that for a 12% (w/v) polymer concentration in the resolving gel one can achieve a gelation time of six minutes (time between crosslinker addition and gelation) if $\overline{M}_w$ is approximately $4.6(10^4)$.

In a preferred embodiment, the new resolving gel ($G_R$) described is used in combination with a polymeric stacking gel ($G_S$). For compatibility, the monomers from which the stacking gel copolymer is made should be the same as, or similar to, those used for the resolving gel. Preferably, acrylamide comprises at least 90 mole percent of the monomer mix. Consequently, the molecular weights, $\overline{M}_n$ and $\overline{M}_w$ of the stacking gel copolymers must be significantly greater than those of the corresponding resolving gel copolymers; preferably, their $\overline{M}_w$ is greater than about 100,000, more preferably greater than about 150,000, suitably about 200,000 or 300,000 and their $\overline{M}_n$ is greater than about 50,000.

The rate of gelation can be expected to increase as (a) the concentration of copolymer in the gel, (b) the molecular weight of the starting copolymer (particularly $\overline{M}_w$), (c) the number of crosslinking sites present per gram of copolymer, and (d) the pH of the solution, increase.

To prevent molecular sieving by the stacking gel, the stacking gel polymer is present at a lower concentration than that of the resolving gel polymer since porosity of the gel is a function of polymer concentration (i.e., average pore size decreases with increasing polymer concentration).

Typically, concentration of the preformed polymer will be from about 8 to about 14%, preferably 10 to 12% (w/v) for the resolving gel and from about 1.5 to about 6%, preferably 2 to 5%, more preferably 2.5 to 4% (w/v) for the stacking gel. For example, the preferred polymer, poly[acrylamide-co-N-(3-chloroacetamidopropyl)methacrylamide] (weight ratio of acrylamide to comonomer: 90/10; mole ratio: 96.5/3.5), is employed at a concentration of about 12% to make a resolving gel, and about 4% to make a stacking gel. However, to ensure gel formation, the molecular weights $\overline{M}_n$ and $\overline{M}_w$ are both higher in the stacking gel polymer than in the resolving gel polymer.

The preferred polymer, poly[acrylamide-co-N-(3-chloroacetamidopropyl)methacrylamide] weight ratio of acrylamide to comonomer: 90/10; mole ratio: 96.5/3.5), preferably has the following molecular weights when used for both purposes:

|  | $\overline{M}_n$ | $\overline{M}_w$ |
| --- | --- | --- |
| Resolving Gel ($G_R$) | $>0.7(10^4)$ | $<10.0(10^4)$ |
| Stacking Gel ($G_S$) | $>5(10^4)$ | $>10.0(10^4)$ |

As indicated earlier, these preferred molecular weights should be similar for any other polymers of structure I that are crosslinked similarly. This is because: 1) the bulk of the polymer composition is derived from acrylamide or modestly substituted acrylamides, 2) the fraction of crosslinking sites per molecule should be similar, and 3) the molecular weight of polymer backbone between crosslinks should also be similar. It is expected therefore that the useful polymers of the invention for forming resolving gels should have an $\overline{M}_n$ of about 7,000 to 30,000 and an $\overline{M}_w$ of about 25,000 to 100,000; and those for forming stacking gels should have an $\overline{M}_n$ of about 50,000 to 300,000 and an $\overline{M}_w$ of about 100,000 to 1,000,000.

Regarding the number of crosslinking sites present on the polymer, whether used as ther resolving or stacking gel, the crosslinking reactions should ideally be done using equal equivalent (i.e., stoichiometric) amounts of reactive crosslinking agent and sites on the polymer. However, we have found it advantageous to use 25–50% more dithiothreitol (or other suitable crosslinking agent) on a chemical equivalency basis than there are crosslinking sites present. The benefits of using 1.25 to 1.5 times the just-required stoichiometric amount of crosslinking agent are (a) better overall crosslinking as manifested by lower degrees of gel swell in high purity water, and (b) assurance that most (if not all) of the electrophilic groups have been reacted. (Unreacted electrophilic groups at potential crosslinking sites could react with nucleophilic groups on proteins and thereby confound the electrophoretic separation process.)

The molecular weights $\overline{M}_n$ and $\overline{M}_w$ can be varied by methods known to those skilled in the synthetic polymer chemistry art. For example, the molecular weights can be decreased by increasing the amount of initiator used, increasing the amount of chain transfer agent used, decreasing the monomer concentration, and increasing the reaction temperature. They can also be varied by selection of the particular chain transfer agent and/or initiator.

The number of equivalents of crosslinking sites per gram of polymer can be varied by adjusting the concentration of monomer(s) from which the 'B— recurring units of structure I are derived. The following examples illustrate the practice of this invention:

EXAMPLE 1

Preparation of a low molecular weight copolymer with an adequate level of crosslinking site to form a resolving gel in about four minutes.

To a 60° C. solution of 2,2'-azobis(methylpropionitrile) (1.0 g) in Milli Q water (i.e., water purified with a Millipore C/N ZD40115-84 unit) (200 mL), isopropanol (20 mL) and conc. sulfuric acid (0.5 g), which had been purged with nitrogen, was added the following solution, which also had been purged with nitrogen: electrophoresis grade acrylamide (64.8 g; 0.91 moles), N-(3-chloroacetamidopropyl)methacrylamide (7.2 g, 0.033 moles), Milli Q water (600 mL), and isopropanol (60 mL), the chain transfer agent. This was added to the first solution dropwise and under nitrogen over a 2-hour period. After the addition was complete, the resultant solution was held for 5 hours more at 60° C. and then allowed to stand at ambient temperature overnight. The next day the solution was concentrated at 40° C. on a rotary evaporator to a volume of about 500 mL. The concentrated solution was then added to 8 liters of reagent grade methanol, with stirring, to precipitate the copolymer. The precipitate was filtered and washed in an additional 4 liters of reagent grade methanol, then dried in a vacuum oven with a nitrogen bleed at 30°-35° C. The yield was 95% based on the original recipe. The inherent viscosity of the copolymer, as determined with a 0.25% solution of the copolymer in aqueous 1.0 molar NaCl at 25° C., was 0.35 dl/g. Cl analysis: theory, 1.55%; found 1.46%. Molecular weight analysis by aqueous size exclusion chromatography showed $\overline{M}_n = 1.51(10^4)$ and $\overline{M}_w = 9.41(10^4)$.

A polymer solution cast from a 12% solution of this copolymer at pH 9.4 began to gel (to a resolving gel) four minutes after addition of the crosslinker (dithiothreitol—44.2 mg per gram of copolymer).

In this and the following examples, the molecular weight averages of the acrylamide/N-(3-chloroacetamidopropyl)methacrylamide copolymers were estimated using an aqueous gel permeation chromatography system in which (a) the fractionation was accomplished with four TSK-GEL (type PW) columns of 6000, 5000, 3000 and 2000 Angstrom permeability limits (Altex Scientific, 1780 Fourth St., Berkeley, Calif. 94710), (b) the eluent was 0.05M $Na_2SO_4$ in 5% ethylene glycol-in-water (v/v), (c) the calibrating standards were Shodex STANDARD P-82 polysaccharides of 853, 380, 186, 100, 48.0, 23.7, 12.2 and 5.8 kDa (Showa Denko K.K., 280 Park Ave., 27th Floor West Building, New York, N.Y. 10017) used at 0.1% (w/v) concentration, (d) the flow rate was 1.5 ml/min and (e) the detection of solute in the column effluent was done refractometrically.

EXAMPLE 2

Preparation of a high molecular weight copolymer with adequate crosslinking site level for forming stacking gels in approximately 40 minutes.

To a 50° C. solution of $(NH_4)_2S_2O_8$ (0.75 g) and $NaHSO_3$ (0.0375 g) in Milli Q water (100 mL) which had been purged of dissolved oxygen by bubbling with nitrogen, was added dropwise in a nitrogen atmosphere over 2 hours the following solution: electrophoresis grade acrylamide (64.8 g; 0.91 moles), N-(3-chloroacetamidopropyl)methacrylamide (7.2 g; 0.033 moles), and $NaHSO_3$ (0.225 g) in Milli Q water (300 mL). The resultant solution was held at 50° C. for an additional hour after the addition of the monomer-containing solution was finished. Then 250 mL more of Milli Q water were added with stirring. The copolymer was precipitated by adding the above solution to 8 liters of reagent grade methanol. The precipitate was filtered, washed and dried (oven at 30°–35° C.). The yield based on the original recipe was 100% and the inherent viscosity of a 0.25% solution of the copolymer in aqueous 1.0 molar NaCl was 1.13 dl/g, which indicates a very high molecular weight copolymer. Cl analysis: theory, 1.55%; found, 1.40%. When a stacking gel is cast from a 4% solution of this copolymer at a pH of 7.8 using dithiothreitol as the crosslinker (44.2 mg per gram of copolymer), gelation occurs 40 minutes after crosslinker addition.

EXAMPLE 3

Preparation of electrophoresis gel

An electrophoresis gel was made with poly[acrylamide-co-N-(3-chloroacetamidopropyl)methacrylamide] (weight ratio of acrylamide to comonomer: 90/10; mole ratio: 96.5/3.5) copolymers disclosed herein. This gel included a lower resolving gel made from poly[acrylamide-co-N-(3-chloroacetamidopropyl)methacrylamide] (weight ratio of acrylamide to comonomer: 90/10; mole ratio: 96.5/3.5) of $\overline{M}_n = 17.8$ kDa and $\overline{M}_w = 78.2$ kDa and a stacking gel from a poly[acrylamide-co-N-(3-chloroacetamidopropyl)methacrylamide] (weight ratio of acrylamide to comonomer: 90/10; mole ratio 96.5/3.5) of Example 2 ($\overline{M}_w \approx 500$ kDa). Each copolymer was crosslinked with dithiothreitol used at 125% of the stoichiometric amount based on the number of crosslinking sites present. The pH of, and buffers used in, the gels and the electrode chambers are summarized in Table I.

TABLE I

| Location | Buffer pH | Composition |
|---|---|---|
| Cathode | 8.3 | 0.025M Tris, 0.192M glycine, 0.1% SDS |
| Stacking gel (4% polymer) | 7.8 | 0.125M Tris.HCl |
| Resolving gel (12% polymer) | 9.4 | 0.375M Tris.HCl |
| Anode | 8.3 | same as cathode except SDS was omitted and 0.1M sodium acetate beneficially added (These variations from cathode conditions are optional.) |

Tris = Tris(hydroxymethyl)aminomethane
SDS = sodium dodecyl sulfate

Tris = Tris(hydroxymethyl)aminomethane
SDS = sodium dodecyl sulfate

In electrophoresis experiments conducted according to the Laemmli procedure with the buffer compositions given in Table I, the dithiothreitol crosslinked poly[acrylamide-co-N-(3-chloroacetamidopropyl)methacrylamide] (weight ratio of acrylamide to comonomer: 90/10; mole ratio 96.5/3.5) copolymers of the present invention perform comparably to gels prepared from acrylamide and N,N'-methylenebisacrylamide. Specifically, the gels prepared from copolymers of this invention permit good electrophoresis separations, with SDS-complexed proteins with molecular weights from about 14.4 kDa to about 200 kDa appearing at the anode and cathode ends of the gel, respectively, after electrophoresis under conditions of voltage and time ordinarily used by those skilled in the art of electrophoresis for SDS-PAGE electrophoresis on acrylamide/bis gel media. Not only is the degree of separation comparable to that achieved with acrylamide/bis-based gels but the sharpness of the separated bands is also very good. These results can be achieved with gels in the so-called "mini" format (0.15 cm×7 cm×8 cm) (thickness×height×width) and in the popular larger format (0.15 cm×16 cm×14 cm).

EXAMPLE 4

Gel solubilization after electrophoresis.

Tas et al. report the solubilization of acrylamide gels crosslinked with DATD or DHEBA with periodic acid. The solubilization of the gel is based on the existence of a —CHOH—CHOH— group in the crosslink chain. The periodic acid breaks the C—C bond and allows the gel to be solubilized [Tas et al., Analytical Biochemistry, 100:264–270 (1979)].

A portion of a gel made from dithiothreitol and poly[acrylamide-co-N-(3-chloroacetamidopropyl)methacrylamide] (weight ratio of acrylamide to comonomer: 90/10; mole ratio: 96.5/3.5) in a pH 9.4 Tris-HCl buffer according to the practice of this invention was immersed in distilled water for 24 hours after the crosslinking reaction was complete. Then, this gel was immersed in a 10 mM solution of periodic acid in water. Within one hour after immersion in the dilute periodic acid solution the gel had vanished and become a solution of the copolymer.

Another portion of the same gel was immersed in water and this portion was entirely intact after such immersion for one hour. Hence, the linkage due to dithiothreitol is cleaved by periodic acid and the polymer that was originally gelled by the crosslinking reaction can be resolubilized by immersion in a dilute periodic acid solution.

Formation of the crosslinked gel in the presence of the Tris-HCl buffer during the DTT crosslinking reaction is proof of the faster reaction of the DTT sulfhydryl groups than of the Tris-HCl amino groups. If this were not so, the polymer would have been capped with the monoamine rather than crosslinked to a gel with the bismercaptan.

EXAMPLE 5 a) Synthesis of high molecular weight copolymer for very low polymer content gels.

Into a reaction vessel held at 50° C. which initially contained a nitrogen-purged solution of 1.5 gram ammonium persulfate dissolved in 400 ml high purity water, were pumped (i) a (previously nitrogen-purged) solution of 259.2 grams of electrophoresis grade acrylamide, 28.8 grams of N-(3-chloroacetamidopropyl)methacrylamide, and 1200 ml of high purity water and (ii) another (nitrogen-purged) solution of 0.525 g sodium bisulfite and 10 ml of high purity water. Solutions (i) and (ii) were added to the reaction vessel over a period of 41 minutes and the combined solutions were held for four hours at 50° C., after which the reaction mixture was permitted to cool to room temperature. Before further use, an additional 500 ml of high purity water were added to this solution, with thorough mixing, to yield a solution that contained 12.5 to 13% (w/v) high molecular weight copolymer.

b) Forming a gel for DNA electrophoresis

To form a gel of very low [2.5% (w/v)] polymer concentration, 1.88 ml of the final solution from Example 5a, 0.5 ml of concentrated TBE buffer [0.2 moles tris(hydroxymethyl)aminomethane (Tris), 0.022 moles boric acid, 0.002 moles ethylenediaminetetraacetic acid and enough high purity water to make 100 ml of solution], 7.59 ml high purity water, 5 microliters of ethidium bromide in water solution (1 mg dye per ml solution) and 26.5 microliters of dithiothreitol in water solution (0.5 g DTT per ml) were mixed well and poured into a shallow plastic tray, the ends of which had been taped in order to contain the copolymer solution. Just after pouring, a multi-toothed plastic well former was inserted into the gel perpendicular to the plane of the gel and perpendicular to the direction of electrophoresis. This assembly was permitted to stand in a covered container (so as to retard evaporation of water) for three hours, after which the gel was overlaid with a TBE solution made by a twenty-fold dilution of the concentrated TBE solution previously described. Then the plastic lane former was carefully removed and the tray (from which the tape at each end was also removed) was inserted into a horizontal electrophoresis cell, to which diluted TBE buffer was added so that the face of the gel was about one mm under the surface of the buffer. Then solutions of undenatured DNA fragments (double-stranded DNA) were loaded into the wells. Electrophoresis at 100 V (voltage gradient about 10 V/cm) for 73 minutes yielded good sample separation and resolution from 123 to at least 1434 base pairs.

The invention has been described in detail with particular reference to preferred embodiments thereof, but it will be understood that variations and modifications can be effected within the spirit and scope of the invention.

We claim:

1. A preformed, acrylamide based, water-soluble copolymer useful for making an electrophoresis medium by crosslinking by a reaction with a selected crosslinking agent that does not involve a free-radical vinyl addition mechanism, said copolymer comprising a minor proportion of a comonomer that contains a site for said crosslinking reaction with said selected crosslinking agent, said preformed copolymer further having the following properties:

1) $\overline{M}_w$ small enough that the addition of 1.25 to 1.5 times the stoichiometric amount of the selected crosslinking agent will not raise the viscosity of the mixture so much that the medium cannot be poured into a 0.15×14×14 cm mold within about 4 to 10 minutes after addition of the crosslinking agent, and 2) $\overline{M}_n$ large enough to provide a crosslink density sufficient to form a gel after about 10 minutes after addition of 1.25 to 1.5 times the stoichiometric amount of the selected crosslinking agent, said gel ultimately having sufficient integrity within about 2 hours after pouring to be removed from the mold and handled gently without tearing or falling apart.

2. The copolymer of claim 1 wherein the number of equivalents of crosslinking sites per gram of copolymer is in the range of $0.45(10^{-4})$ to $14(10^{-4})$.

3. The copolymer of claim 2 wherein said number of equivalents is at least $2/\overline{M}_n$.

4. The copolymer of claim 2 wherein said number of equivalents is from about $2.25(10^{-4})$ to $10(10^{-4})$.

5. The copolymer of claim 1 wherein said $\overline{M}_w$ is such that said addition of said crosslinking agent will not raise the viscosity so much that the medium cannot be poured into said mold within about 6 to 8 minutes after said addition.

6. The copolymer of claim 2 wherein said number of equivalents is from about $4(10^{-4})$ to $7(10^{-4})$.

7. The copolymer of claim 1 which is a water soluble vinyl addition copolymer derived from a mixture of monomers comprising from 85-98 mole percent of a first monomer selected from acrylamide and the N-substituted acrylamides wherein the N-substituent is an alkyl group having from 1 to 5 carbon atoms; from 2 to 15 mole percent of a second, vinyl monomer having a reactive group selected from the group consisting of a) active halogen groups; b) activated 2-substituted ethylsulfonyl or activated vinylsulfonyl groups; c) epoxy groups; d) isocyanate groups; e) aziridine groups; f) aldehyde groups; g) 2-substituted ethylcarbonyl groups; and h) succinimidoxycarbonyl groups; and from 0 to 12 mole percent of one or more other polymerizable nonionic vinyl monomers selected from styrene monomers, acrylic monomers, methacrylamide monomers and N-substituted acrylamide monomers wherein the substituent contains at least 6 carbon atoms.

8. The copolymer of claim 7 which comprises from 90 to 97 mole percent of said first monomer.

9. The copolymer of claim 7 which comprises from 3 to 10 mole percent of said second monomer.

10. The copolymer of claim 1 wherein said copolymer has a number average molecular weight, $\overline{M}_n$, of at least about 7,000 and a weight average molecular weight, $\overline{M}_w$, of less than about 100,000.

11. The copolymer of claim 10 wherein said $\overline{M}_n$ is from about 7,000 to about 30,000.

12. The copolymer of claim 10 wherein said $\overline{M}_w$ is from about 25,000 to about 100,000.

13. A method of preparing an electrophoresis gel in situ which comprises mixing an aqueous solution of a copolymer of claim 1 with a selected crosslinking agent that will react with crosslinkable sites on said copolymer by a reaction with a selected crosslinking agent that does not involve a free-radical vinyl addition mechanism.

14. The method of claim 13 wherein the number of equivalents of crosslinking sites per gram of copolymer is in the range of $0.45(10^{-4})$ to $14(10^{-4})$.

15. The method of claim 13 wherein said copolymer has a number average molecular weight, $\overline{M}_n$, of at least about 7,000 and a weight average molecular weight, $\overline{M}_w$, of less than about 100,000.

16. The method of claim 13 wherein said $\overline{M}_n$ is from about 7,000 to about 30,000.

17. The method of claim 13 wherein said $\overline{M}_w$ is from about 25,000 to about 100,000.

18. The method of claim 13 wherein said copolymer is present in said solution in a concentration of from about 8 to about 14% w/v.

19. The method of claim 13 wherein said copolymer is present in said solution in a concentration of from about 1.5 to about 6% w/v.

20. The method of claim 18 wherein said concentration is from about 10 to 12%.

21. The method of claim 19 wherein said concentration is from about 2 to 5%.

22. The method of claim 19 wherein said concentration is from about 2.5 to 4%.

23. The method of claim 13 wherein the crosslinking agent is selected from the group consisting of compounds having two or more reactive groups selected from amino, mercapto and phenolic hydroxy.

24. The method of claim 13 wherein the crosslinking agent is selected from the group consisting of ethylenediamine, 1,3-propanediamine, 1,3-propanedithiol, dithiothreitol, dithioerythritol, 1,5-pentanediamine, hexamethylenediamine, diethylenetriamine, triethylenetetramine, propylenediamine, di(aminomethyl)ether, 1,8-diamino-4-(aminomethyl) octane, xylylenediamine, hydroquinone, bisphenol A, bisphenol sulfone, 1,4-butanedisulfinic acid, benzenedisulfinic acid, thioethanolamine, p-aminothiophenol and butylenediamine.

25. The method of claim 13 wherein the crosslinking agent is dithiothreitol.

26. An electrophoresis element which comprises a resolving gel comprising a crosslinked copolymer of claim 10.

27. An electrophoresis element which comprises a stacking gel and a resolving gel, said stacking gel comprising a crosslinked copolymer of claim 13 and said resolving gel comprising a crosslinked copolymer of claim 10.

28. A kit for electrophoresis which comprises a copolymer of claim 1, and, in a container separate from said copolymer, a crosslinking agent for crosslinking said copolymer by a reaction that does not involve a free-radical vinyl addition mechanism.

29. The kit of claim 28 which comprises a copolymer of claim 10.

30. The kit of claim 29 which further comprises a copolymer of claim 13.

31. The kit of claim 28 wherein said crosslinking agent is dithiothreitol.

* * * * *